United States Patent
Hsieh et al.

(10) Patent No.: US 6,850,585 B2
(45) Date of Patent: Feb. 1, 2005

(54) PROGRESSIVE UPDATING APPROACH FOR VOLUMETRIC CT IMAGE RECONSTRUCTION

(75) Inventors: Jiang Hsieh, Brookfield, WI (US); Ge Wang, Iowa City, IA (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 142 days.

(21) Appl. No.: 10/382,154

(22) Filed: Mar. 5, 2003

(65) Prior Publication Data

US 2004/0174960 A1 Sep. 9, 2004

(51) Int. Cl.⁷ .............................................. A61B 6/03
(52) U.S. Cl. .............................. 378/4; 378/15; 378/901
(58) Field of Search ........................... 378/4, 8, 15, 19, 378/901

(56) References Cited

U.S. PATENT DOCUMENTS

| | | | |
|---|---|---|---|
| 6,246,742 B1 * | 6/2001 | Besson et al. | 378/8 |
| 6,366,638 B1 | 4/2002 | Hsieh et al. | |
| 6,381,297 B1 | 4/2002 | Hsieh | |
| 6,385,278 B1 | 5/2002 | Hsieh | |

* cited by examiner

Primary Examiner—David V. Bruce
(74) Attorney, Agent, or Firm—Artz & Artz, PC (57) ABSTRACT

In overlapping reconstruction for multi-slide spiral CT, adjacent slices of an object typically only have small differences. Based on this property, a progressive updating approach for volumetric ct image reconstruction includes a method and apparatus to use the well-known ordered subset expectation maximization (OSEM) formula or other iterative algorithms for spiral CT overlapping reconstruction. The imaging geometry is assumed to be single-slice helical/spiral scanning. To start with, a complete set of projections is synthesized via linear interpolation of data associated with opposite rays for reconstruction of the first slice. Then, new data are incrementally utilized for reconstruction of subsequent slices by updating the previous slice using the OSEM approach. To overcome accumulative errors, traditional reconstruction from a complete set of projections is performed when it is necessary as is determined by dynamically monitoring the relevant errors.

18 Claims, 5 Drawing Sheets

PROGRESSIVE UPDATING APPROACH FOR VOLUMETRIC CT IMAGE RECONSTRUCTION

TECHNICAL FIELD

The present invention relates generally to imaging systems and more particularly to X-ray computed tomography.

BACKGROUND

X-ray computed tomography or CT is a method of imaging the inside of the body using an x-ray beam. As the x-ray flux passes through the body, it is absorbed by bones, tissues, fluid, etc. within the body, thereby varying resultant flux intensity. The intensity of the x-ray flux emerging from the body is measured by detectors, and then the data are reconstructed into a detailed picture.

Multi-slice CT scanners are special CT systems equipped with a multiple-row detector array rather than a single-row detector array. This allows for simultaneous scan of multiple slices at adjacent locations.

A typical CT scanner includes a gantry having an annular frame for supporting an annular disk about a rotation or scanning axis of the scanner. The disk includes a central opening large enough to receive a patient extending along the scanning axis, and the disk is rotated about the patient during a scanning procedure. An x-ray tube is positioned on the disk diametrically across the central opening from an array of x-ray detectors. As the disk is rotated, the x-ray tube projects a flux of energy, or x-rays, along a scan plane, through the patient, and to the detector array. By rotating the x-ray source about the scanning axis and relative to the patient, x-rays are projected through the patient from many different directions. An image of the scanned portion of the patient is then reconstructed from data provided by the detector array using a computer.

In multi-slice CT reconstruction, it is a common practice that overlapping reconstruction is performed. That is, adjacent transverse slices have a significant overlap so that the inherent longitudinal image resolution can be utilized. Traditional methods for overlapping reconstruction are based on filtered back-projection, and are quite time-consuming and noise sensitive.

In CT fluoroscopy, CT images of a particular location or fixed volume are continuously generated to provide real time feedback to the CT operators. This currently requires a patient to be scanned continuously to update a complete dataset during the entire procedure. It is desirable, however, to be able to produce updated images with projections less than the complete dataset.

In bolus chasing for CT angiographic studies, a set of preparatory scans is acquired at a particular location to monitor the arrival of a contrast agent. When the contrast level reaches a pre-determined threshold, helical scans are initiated. If partial projections can be used to produce images, a significant dose minimization will result from the preparatory scans.

A disadvantage of the aforementioned current systems is that the reconstruction algorithms essentially rely on complete projection datasets to produce an image (180° for parallel flux and 180 plus a fan angle for fan beam flux). Images reconstructed with these algorithms require higher x-ray dose and are subject to degraded temporal resolution and increased noise.

The disadvantages associated with current CT systems have made it apparent that a new technique for CT scanning and image reconstruction is needed. The new technique should substantially increase information acquired from each patient while minimizing the required amount of data or scan dose. The present invention is directed to these ends.

SUMMARY OF THE INVENTION

In accordance with one aspect of the present invention, a host computer for an imaging system having a scanning unit includes a reconstruction controller adapted to command the scanning unit to conduct a first scan of a complete projection dataset thereby generating the first image. The controller is further adapted to command the scanning unit to conduct a second scan and generate the second image. The second scan is adapted to be less than a complete projection dataset scan. The second scan is also adapted to include the first image as an initial condition.

In accordance with another aspect of the present invention, a reconstruction method for an imaging system includes conducting a first scan for a complete projection dataset and generating the first image from the first scan. The second scan is conducted and the second image is generated from the second scan. The second scan is adapted to be substantially less than a complete scan and is adapted to include the first image as an initial condition. Then, the third scan is performed and the third image is generated from the third scan based on the second image with the third scan containing a relatively small additional amount of projections.

In accordance with yet another aspect of the present invention, a complete scan is performed from time to time or location to location to minimize accumulative error introduced by the progressive updating scheme. The duration between the occasional complete scan depends on the scanned object (different shape and part of anatomy, different contrast dynamics) and the scanning protocols (helical pitch, detector aperture, number of detector rows, reconstruction method and parameters, etc.)

One advantage of the present invention is that it uses a relatively smaller amount of incremental data from an object of interest with reduced dose as compared to the existing art. The key is to reconstruct an image only from less than complete data based on a strong knowledge represented by its spatially and/or temporally neighboring image, even if the image variation is not spatially localized.

Additional advantages and features of the present invention will become apparent from the description that follows and may be realized by the instrumentalities and combinations particularly pointed out in the appended claims, taken in conjunction with the accompanying drawings, or be realized with modifications in the same spirit of this patent document.

BRIEF DESCRIPTION OF THE DRAWINGS

For a more complete understanding of the invention, there will now be some embodiments thereof, given by way of example, reference being made to the accompanying drawings, in which.

DETAILED DESCRIPTION

The present invention is illustrated with respect to a Computed Tomography (CT) scanning system 10, particularly suited to the medical imaging field. The present invention is, however, applicable to various other uses that may require tomographic scanning, as will be understood by one skilled in the art.

The present invention makes use of the fact that most of the spatially and/or temporarily neighboring images in a scan series differ only slightly from each other, where the differences are not necessarily spatially localized. Therefore, a new image is generated based on the previously reconstructed images and a sub-set of additional new projections to update the changes in the image. In other words, existing images are used as the initial condition or basis for the estimation of the next image. Since a majority of the pixels do not change much between neighboring images, only a small amount of projections are needed to "update" the pixels in the old image to produce a new image.

The present invention makes use of the well-know ordered-subset (OS) expectation maximization (EM) algorithm to implement the idea of the progressive updating approach for volumetric CT image reconstruction, while other OS-type methods may also be used for the same purpose. In a CT problem, the section/volume can be partitioned into n pixels/voxels, each of which has a constant X-ray attenuation factor $x_j$, j=1, . . . , n. Assuming that projection data are associated with m rays, $b_i$, i=1, . . . , m. The following linear system occurs: Ax=b, where A=($a_{ij}$).

The EM formula for inverting this system is:

$$x_j^{(k+1)} = \frac{x_j^{(k)}}{\sum_{i=1}^{m} a_{ij}} \sum_{i=1}^{m} \frac{a_{ij} b_i}{\langle a_i, x \rangle}, j = 1, \ldots, n.$$

The OSEM formula can be expressed as:

$$x_j^{(k,i)} = \frac{x_j^{(k,i-1)}}{\sum_{l \in S_i} a_{lj}} \sum_{l \in S_i} a_{lj} \frac{b_l}{\langle a_l, x^{(k,i-1)} \rangle}, i = 1, \ldots, p; j = 1, \ldots, n.$$

It is emphasized that other iterative algorithms are also possible, such as those discussed in the article, "Development of Iterative Algorithms for Image Reconstruction," Ming Jiang and Ge Wang, to appear in the *Journal of X-ray Science & Technology: A Special Issue on Clinical Applications of Modern Imaging Technologies*.

Figure 1:
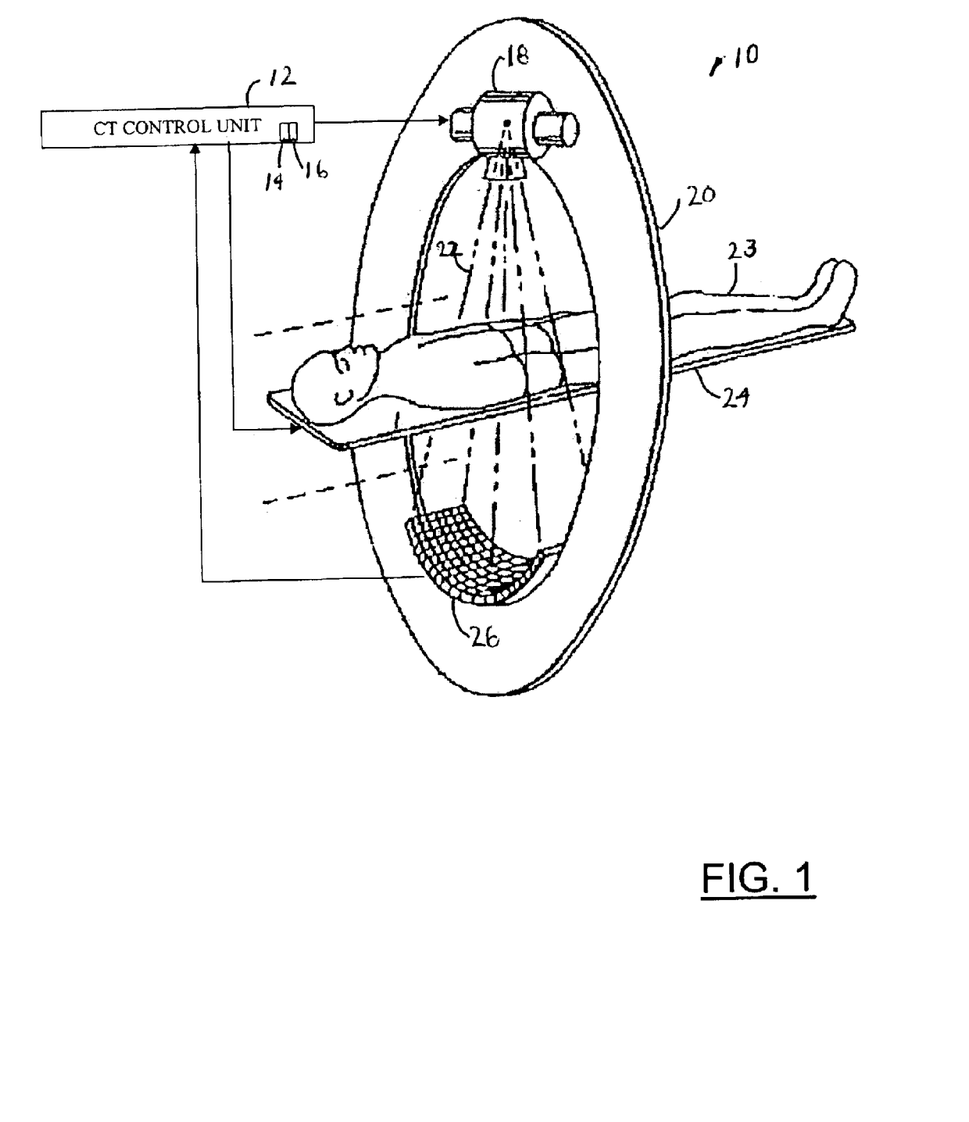
FIG. 1 is a diagram of an imaging system in accordance with a preferred embodiment of the present invention.
Figure 2:
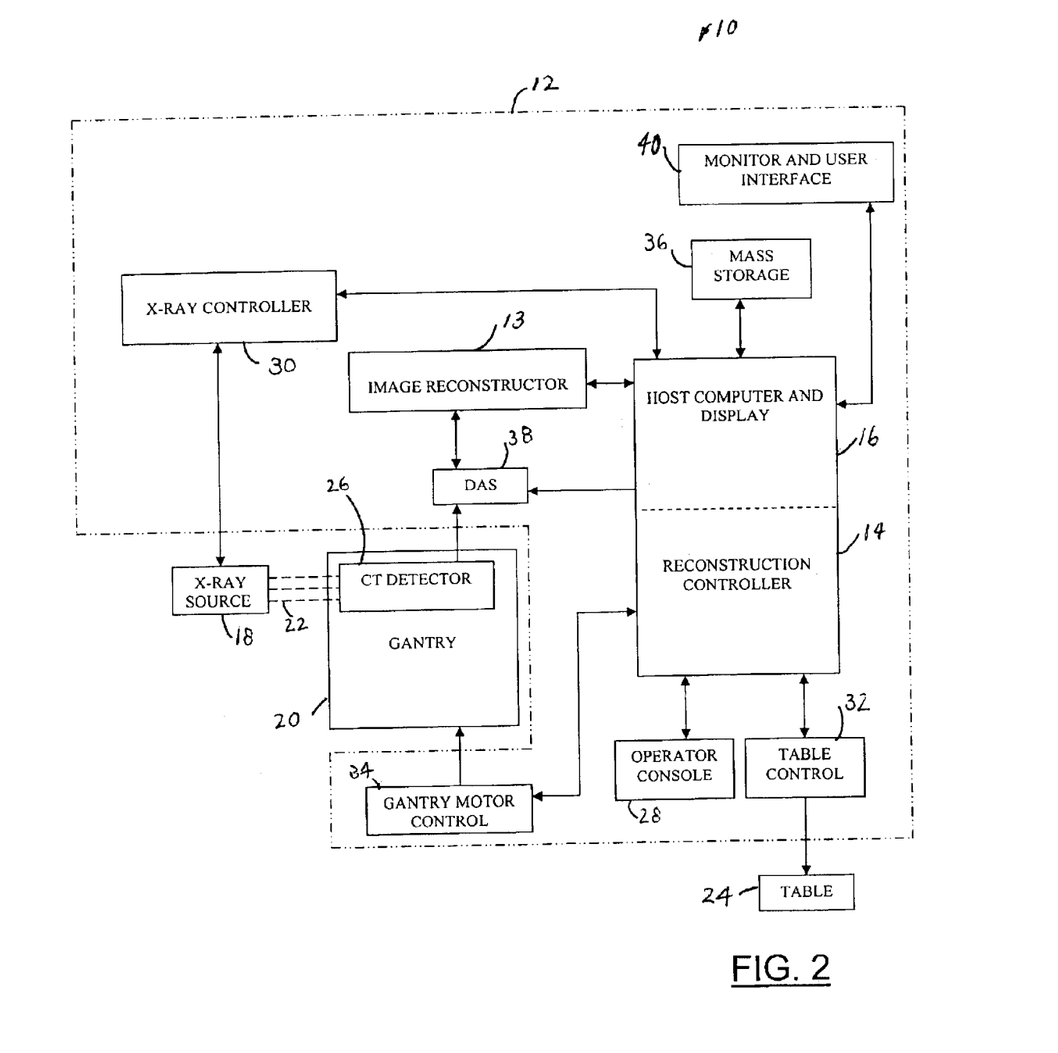
FIG. 2 is a partial block diagram of FIG. 1.

Referring to FIGS. 1 and 2, an imaging system 10 including a CT control unit 12, in accordance with a preferred embodiment of the present invention, is illustrated. The CT control unit 12 includes an image reconstructor 13 coupled to a host computer and display 16. The host computer and display 16 includes a reconstruction controller 14. The CT control unit 12 further includes various other known CT elements also coupled to the host computer and display 16, as will be discussed later. An x-ray source 18, which is coupled to the CT control unit 12, is also coupled to a gantry 20. The x-ray source 18 generates an x-ray flux 22, which passes through an object 23 (e.g. a patient) on a table 24. The system 10 further includes a CT detector array 26, coupled to the gantry 20, which generates detector signals in response to the x-ray flux 22. The CT control unit 12 is coupled to the detector array 26 and receives detector signals, which are also referred to as raw projection data.

The CT control unit 12 also includes, for example, an operator console 28, an x-ray controller 30, a table control 32, a gantry motor control 34, a mass storage 36, and a data acquisition system 38, all of which will be discussed later.

The host computer and display 16, within the CT control unit 12, receives the detector signals through the image reconstructor 13. The host computer and display 16 contains logic (the reconstruction controller 14) that progressively updates CT images in response to the signals from the image reconstructor 13.

The reconstruction controller 14 commands the first scan for a complete projection dataset for the reconstruction of the first image. The complete projection dataset spans 180° plus fan angle, or it can also contain 360° of projections. Subsequently, the controller 14 reconstructs the first image, and commands the second scan, which is substantially less than a complete scan, for example, involving half of the minimum projections. The second scan uses the first image as an initial condition to generate the second image. When the first two images differ by a relatively small distance (as the case of a helical scan) or by a relatively small time span (as the case of a cine scan), the amount of difference between the two images is relatively small. Then, the third image is reconstructed based on the second image and an additional, relatively small, amount of projections. This procedure can be repeated multiple times for reconstruction of subsequent images.

The image reconstructor 13 is coupled to the host computer and display 16 and the Data Acquisition System (DAS) 38. The image reconstructor receives detector signals from the DAS 38, or alternately directly from the detectors 26, and generates CT images.

The gantry 20 is the ring shaped platform within which the source and the detector array rotates around the scanned object 23 in response to signals from the gantry control 34, as will be understood by one skilled in the art. Typically, the x-ray source 18 and the (multi-slice) detector array 26 are coupled thereto.

The x-ray source 18 is embodied as a distributed x-ray source, an extended x-ray source (e.g. Imatron), or a standard x-ray tube. The x-ray source 18 is activated by either a host computer 16 or an x-ray controller 30, as will be understood by one skilled in the art. The x-ray source 18 sends the x-ray flux 22 through an object 23 on a moveable table 24 controlled by a control device 32 acting in response to signals from the host computer 16, as will be understood by one skilled in the art.

The x-ray flux 22 from the x-ray source 18 passes through the patient and impinges on the x-ray detector 26. The signal passes to the host computer and display 16, where the signal is converted to a gray level corresponding to the linear attenuation coefficients of the patient using appropriate pre-processing and reconstruction methods.

The detector array 26 is typically located opposite the x-ray source 18 to receive x-ray flux 22 and includes several modules. The host computer 16 receives the detector signal and typically activates the x-ray source 18.

Data is acquired and processed, and a CT image, for example, is presented to a radiologist through the monitor and user interface 40 while the scan is occurring. The host computer 16 needs only read the module signals and update the display through the image reconstructor 13 and data acquisition system (DAS) 38. The host computer 16 can store image data in a mass storage unit 36 for future reference.

The present invention is illustrated with respect to x-ray computed tomography (CT) systems, however it is alternately used for any type of imaging system including, magnetic resonance imaging (MRI), mammography, vascular x-ray imaging, positron emission tomography (PET), ultrasound, optical imaging, etc. Further embodiments include non-medical applications such as weld inspection and metal inspection. Essentially, anything that could use an imaging system to make multi-dimensional images.

The first advantage of the proposed approach is the reduction x-ray dose to patient. Using the prep scan as an example, the images in the prep scans represent the patient anatomy of the same location. The only difference between the first image and the consecutive images are the amount of contrast agent uptake by the organs. As is discussed previously, there is no need to perform complete scans (180° plus a fan angle) to estimate the status of the contrast uptake. Based on the first image, only a fraction of the full projection set (e.g., 90° of projection) is needed to generate the second image. This is a factor of two in dose reduction. Similarly, if a third image is required, only additional 90° of projection is needed with the second image. Depending on the differences between the consecutive images, the amount of projections can be either larger or smaller than 90°. This concept can be applied to both the helical data acquisition mode as well as step-and-shoot or cine mode.

Another example of the dose reduction application is the production of images pre and post contrast injection. Once the contrast-free images are generated, the images with contrast can be generated with scans of much higher helical pitch or coarser angular sampling. Since the difference between the two imaging volume is caused by the contrast uptake, less projection data (e.g., higher helical pitch) is alternately used to estimate the difference. Since much higher helical pitch is used, the x-ray dose is reduced, provided that other conditions are substantially identical.

Another advantage of the progressive updating approach is improving the temporal resolution of the scanner during, for example, a cardiac study. To perform coronary artery imaging (CAI), the heart volume is scanned. If no contrast agent is present, multi-sector type of reconstruction can be used (The complete projection dataset is acquired over several cardiac cycles at the same cardiac phase). The temporal resolution is quite high. With contrast agent, the multi-sector reconstruction is less effective. The image difference is limited to a small region, and the difference is small between the cardiac images taken with and those taken without contrast. Therefore, based on the contrast-free images and a small fraction of the projection data with contrast (e.g., projection data over a 90° range collected over a single cycle of the heart), cardiac images with contrast are obtained. Since the data is acquired over a shorter period of time, improved temporal resolution is obtained.

The third advantage of the progressive scan is to reduce the computational complexity of image production. The primary example is the use of the progressive updating method for overlapping reconstruction in spiral CT. In overlapping reconstruction, adjacent slices differ little. Instead of reconstructing each slice independently, the progressive updating method effectively utilizes the correlation between the slices. CT fluoroscopy is used as another illustrative example. Once the first image is generated, the next image is generated by updating the first image with a small fraction of the new projections. Since the number of projection needs to be processed is a small fraction of the full dataset, the amount of computation can be significantly reduced.

To demonstrate the feasibility of the OSEM algorithm for overlapping reconstruction in spiral CT, numerical simulations were performed using the three-dimensional Shepp-Logan head phantom. In the simulation, both the detector collimation and the table increment per source rotation were set to 1. The detector array consisted of 128 cells, and 120 projections were collected per source rotation. The reconstruction matrix of the phantom is 128 by 128 by 128, just containing the phantom. Also, the gray-levels of the original and reconstructed images are linearly transformed for better visualization, mapping the interval [0.95, 1.05] into 256 gray levels with necessary truncation.

In the initial test, 75% is assumed for overlapping reconstruction (distance between adjacent slices is one quarter of the collimator aperture). The first slice is reconstructed at $z_0$ from a complete set of projection data synthesized from helical data. Then, this slice is treated as the input to reconstruct the slice at $z_0+0.25$. After that, the slice at $z_0+0.25$ is used as the input to reconstruct the slice at $z_0+0.5$, and so on.

Because the first slice is the initial input to the reconstruction algorithm, it should be reconstructed with a sufficiently high precision. The two common interpolation algorithms utilize identical and opposite orientation rays, respectively. Because of the superior slice sensitivity profile of the opposite ray interpolation method, the OSEM is used in combination with that interpolation method to reconstruct the first slice.

After the first slice is reconstructed using the opposite ray interpolation method, reconstruction of subsequent slices is performed using the OSEM method. To illustrate the present invention, three data selection methods are discussed, which do not involve data interpolation for the OSEM based overlapping reconstruction: the first method is the reconstruction of a slice using the nearest data of 180 degrees. For a certain slice position z, there are two sub-datasets that are respectively above and below the slice at z, each spanning 90°. The second method is the reconstruction of a slice using 90° data being evenly distributed above and below the slice respectively. For a certain slice position z, there are two sub-datasets that are respectively above and below the slice at z, each spanning 45°. Heuristically, these two sub-datasets are most relevant to the slice of interest. The third method is the reconstruction of a slice using the nearest data of 90° above the slice. This portion of data is not used in the previous reconstruction.

Let d(m,n) denote the difference of a reconstructed slice and the original slice at the location (m,n):

$$d(m,n)=\text{RecImg}(m,n)-\text{OrigImg}(m,n),$$

with RecImg(m,n) and OrigImg(m,n) as the reconstructed and original slices, respectively. Then, the accuracy of the image reconstruction can be measured as:

$$RSD = \sqrt{\sum_{m=0}^{M-1}\sum_{n=0}^{N-1}[d(m,n)]^2},$$

which yields the root of the sum of squared differences (RSSD) per slice. Furthermore, the mean RSSD is defined as:

$$MRSSD = \frac{1}{M \cdot N} RSSD,$$

which captures the discrepancy between the reconstructed slice and the actual slice.

Regular reconstruction (reconstruction using the OSEM with a set of complete projection data synthesized via opposite ray interpolation) may be needed to suppress accumulative reconstruction errors when they become significant. This is because the OSEM based overlapping reconstruction is an iterative procedure, and the artifacts of current slice may be transferred to the next slice. According to a preliminary experiment, when the phantom size changes greatly, the regular reconstruction should be done more frequently than in other cases. This process can be automated by dynamically monitoring the errors between measured and synthesized projection data.

For example, the difference between projections that are 360° apart can be examined. When the shape of the object does not change quickly, the difference is small. The difference of conjugate samples that are 180° apart can be alternately utilized. In either method, a mapping is provided to determine the regular reconstruction interval based on the projection error, which is application-dependent. Alternately, regular images can be generated at a very coarse interval. Based on the difference between the images reconstructed, the frequency of the regular images can be adjusted.

To test the noise property simultaneously, various types of noise are added. For example, uniform noise is added within the interval (0.0, 2.0) in projections. Then, the image quality is evaluated by signal to noise ratio (SNR). Assuming $$S = \frac{\sum_{m=0}^{M-1}\sum_{n=0}^{N-1}[(\text{Orig } Im\ g(m,n) - \text{Mean } Im\ g)^2]}{M \cdot N} \text{ and}$$

$$N = \frac{\sum_{m=0}^{M-1}\sum_{n=0}^{N-1}[(\text{Orig } Im\ g(m,n) - \text{Rec } Im\ g(m,n))^2]}{M \cdot N}$$

where MeanImg is the mean value of original slice. Then, $$SNR = 10 \times 1g\left(\frac{S}{N}\right).$$

Figure 3:
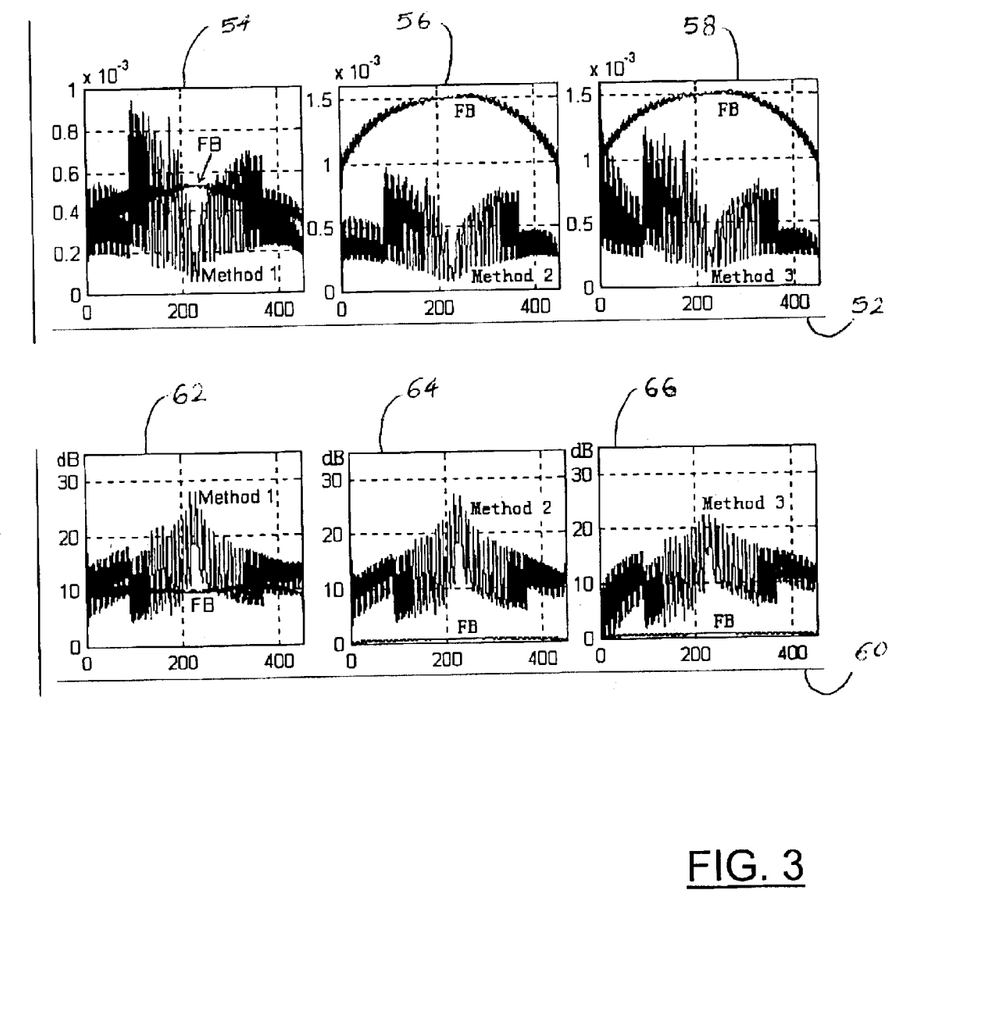
FIG. 3 illustrates the MRSSD versus the slice index and the SNR versus the slice index in accordance with another embodiment of the present invention.

In the following experiments, the three methods were compared (with only one iteration) with FB (Filtered Backprojection) respectively using the corresponding projection data. This comparison was performed slice by slice for the whole phantom. The subset size of OSEM is 20, and the regular reconstruction used is illustrated in FIG. 3. In FIG. 3, the first row of plots 52 includes MRSSD versus the slice index for the first method 54, the second method 56 and the third method 58 respectively, while the second row of plots 60 includes SNR versus the slice index for the first method 62, the second method 64 and the third method 66 respectively.

Figure 4:
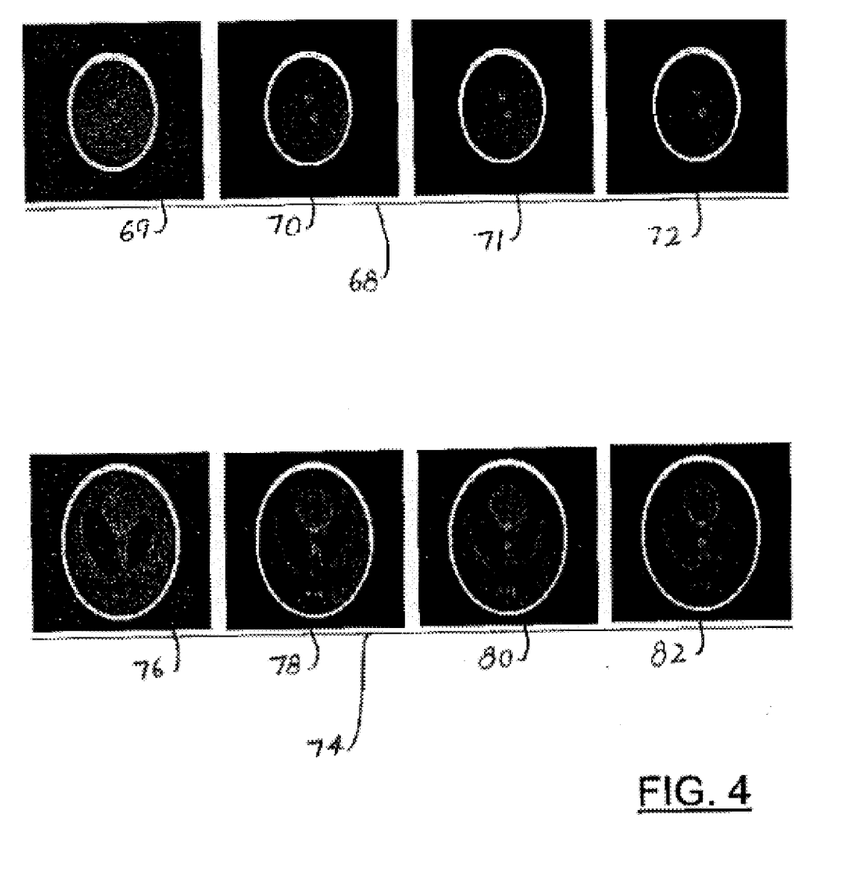
FIG. 4 is two transaxial slices and reconstructed counterparts in accordance with the above embodiment of the present invention.

Referring to FIG. 4, two transaxial slices and reconstructed counterparts are illustrated. Some representative experimental results are shown in FIG. 4, which do not include the slices by regular reconstruction. The first row 68 of images includes, (SNR=10.74 dB, MRSD=4.05×10$^{-4}$) 69, (SNR=14.71 dB, MRSD=2.58×10$^{-4}$) 70, (SNR=14.45 dB, MRSD=2.65×10$^{-4}$) 71, and (SNR=11.23 dB, MRSD=3.91×10$^{-4}$) 72. The second row 74 of images includes, (SNR=10.41 dB, MRSD=4.89×10$^{-4}$) 76, (SNR=19.58 dB, MRSD=1.70×10$^{-4}$) 78, (SNR=19.29 dB, MRSD=1.76×10$^{-4}$) 80, and (SNR=18.35 dB, MRSD=1.96×10$^{-4}$) 82.

The first row 68 corresponds to the 100th slice, while the second row 74 corresponds to the 320th slice. In the first column 69, 76 is the reconstruction using FB with the data selection that is same with the first method, while the subsequent columns show the reconstructed results using the three data selection methods respectively.

According to the above results, the performance of the three methods is superior to that of FB. Because the first method uses more complete projection data than the second method and the third method, it performs better in terms of image quality over the latter two methods, but the differences are not too significant because a small pitch is used.

Furthermore, these three methods require only one iteration. The computation time of one complete iteration cycle of OSEM is comparable to that of FB algorithm in our experiments, but FB with the corresponding data produced poor image quality. Since the data used in the second method and the third method are only half of that in the first method, the second method and the third method are much faster than FB practically if the regular reconstruction is not considered.

Figure 5:
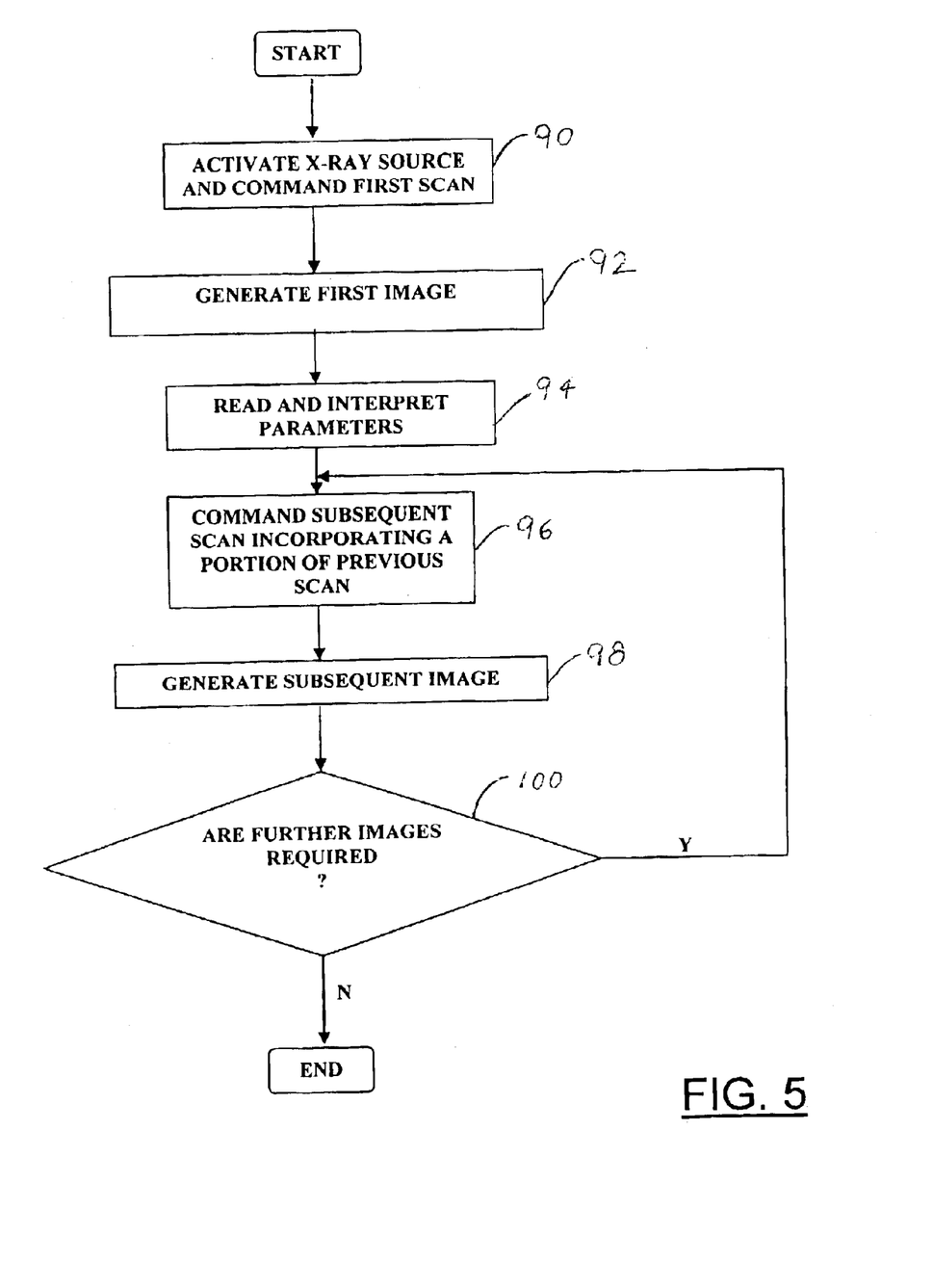
FIG. 5 is a block diagram of a method for image reconstruction, in accordance with the above embodiment of the present invention.

Referring to FIG. 5, a block diagram of a method for image reconstruction, in accordance with the above preferred embodiment of the present invention, is illustrated. Logic starts in operation block 90 where the x-ray source is activated and the first scan is commanded by the host computer. The first scan is typically a complete dataset.

In operation block 92, the first image is reconstructed.

In operation block 94, specific parameters for progressive updating are obtained.

In operation block 96, a subsequent scan is generated, which can incorporate a portion of the previous scan or can be independent of the previous scan.

In operation block 98, the image from the scan of operation block 96 is generated.

In inquiry block 100, a check is made whether further detector signals are required to update the image for useful information on the object undergoing the scan. For a positive response, operation block 96 reactivates, and a subsequent scan is commanded. Otherwise, the method concludes.

In operation, an imaging system generates the first image using a complete projection dataset. The progressive update approach is then activated to generate subsequent images. The first image is generated using a current reconstruction method. That is, a complete projection dataset (typically 180° plus fan angle) is used for the reconstruction. The next image uses, for example, 90° of projections with the first image as the initial condition. thence, the production of the second image uses only half of the minimum projections. Since the two images differ by a small distance (a quarter of the slice thickness in this case), difference between the two images is small. It requires only a small amount of projections to generate the new image. The third image is generated based on the second image with additional 90° projection data. This process continues until a satisfactory series of images are generated.

The host computer cycles typical signal processing steps in response to the detector signals, as will be understood by one skilled in the art. In other words, data offsets are corrected for line integrals through the field of view. Necessary calibration corrections are made, and the resulting data is processed to reconstruct an image. The image is then converted to display pixel format for subsequent viewing and analysis.

From the foregoing, it can be seen that there has been brought to the art a new imaging system and methodology. It is to be understood that the preceding description of the preferred embodiment is merely illustrative of some of the many specific embodiments that represent applications of the principles of the present invention. Numerous other arrangements would be evident to those skilled in the art without departing from the scope of the invention as defined by the following claims.

What is claimed is:

1. A computer for an imaging system having a scanning unit comprising:
   a controller adapted to command the scanning unit to conduct the first scan of a complete projection dataset thereby generating a first image, said controller further adapted to command the scanning unit to conduct a second scan and there from generate a second image, said second scan adapted to be significantly less than a complete projection dataset scan, said second scan adapted to include said first image as an initial condition.

2. The system of claim 1, wherein said controller comprises one of a computed tomography controller, a magnetic resonance imaging controller, a mammography controller, a vascular x-ray imaging controller, a positron emission tomography controller, a single photon emission computed tomography controller, an ultrasound controller, an optical imaging controller, or other controllers similar thereto.

3. The system of claim 1, wherein said second scan is significantly less than a complete projection dataset.

4. The system of claim 1, wherein said reconstruction controller is further adapted to command the scanning unit to conduct a third scan, said third scan adapted to generate a third image based on said second image with additional projections significantly less than a complete data set.

5. The system of claim 1, wherein said controller generates said first image through commanding the scanning unit to generate an x-ray flux which is received in a detector array, which generates detector signals, said detector signals are received in an image reconstructor, which generates said first image signal.

6. The system of claim 1 wherein said first image is a contrast-free CT image, and said second image includes contrast and is generated with at least one of a substantially higher helical pitch or a lower sampling rate than said first scan.

7. The system of claim 1 wherein said first image and second image are acquired in either a helical mode or a cine mode.

8. A reconstruction method for an imaging system comprising:
   generating a first scan as a complete projection dataset;
   generating a first image from said first scan; and
   generating a second scan;
   generating a second image from said second scan, said second scan adapted to be substantially less than a complete scan and adapted to include said first image as an initial condition.

9. The method of claim 8 further comprising generating a third scan;
   generating a third image from said third scan based on said second image with a relatively small additional amount of projections.

10. The method of claim 8 wherein generating said first scan further comprises generating said first scan and generating said first image, wherein said first image is a contrast-free image.

11. The method of claim 8 wherein, generating said second image from said second scan further comprises generating said second image, including a contrast, with at least one scan having at least one of a substantially higher helical pitch or a lower sampling rate than said first scan.

12. The method of claim 8 further comprising generating a temporal image from said first image, said second image, and said third image.

13. The method of claim 8 further comprising generating a periodic "refresh" with appropriate complete projection dataset.

14. The method of claim 8 further comprising automatically estimating at least one of a refreshing or updating frequency.

15. A reconstruction method for an imaging system comprising:
   generating a first scan for a complete projection dataset;
   generating a first image from said first scan;
   generating a second scan;
   generating a second image from said second scan, said second scan adapted to be substantially less than a complete scan and adapted to include said first image as an initial condition;
   generating a third scan; and
   generating a third image from said third scan based on said second image with a relatively small additional amount of projections.

16. The method of claim 15 further comprising generating said first image, wherein said first image is a contrast-free image.

17. The method of claim 15 wherein generating said second image further comprises generating said second image, including a contrast, with at least one scan having at least one of a substantially higher helical pitch or lower sampling rate than said first scan.

18. The method of claim 15 further comprising generating a temporal image from said first image, said second image signal, and said third image signal.

* * * * *